(12) United States Patent
Kemp

(10) Patent No.: US 11,039,979 B2
(45) Date of Patent: Jun. 22, 2021

(54) PERSONAL THERAPY DEVICE UTILIZING SHAPE TRANSFORMATION AND ADVANCED MOTION CONTROL

(71) Applicant: Michael Kemp, Martinsburg, WV (US)

(72) Inventor: Michael Kemp, Martinsburg, WV (US)

( * ) Notice: Subject to any disclaimer, the term of this patent is extended or adjusted under 35 U.S.C. 154(b) by 294 days.

(21) Appl. No.: 16/408,393

(22) Filed: May 9, 2019

(65) Prior Publication Data

US 2019/0343715 A1 Nov. 14, 2019

Related U.S. Application Data

(60) Provisional application No. 62/670,652, filed on May 11, 2018.

(51) Int. Cl.
*A61H 19/00* (2006.01)
*A61L 31/14* (2006.01)
*A61L 31/02* (2006.01)

(52) U.S. Cl.
CPC ............ *A61H 19/44* (2013.01); *A61L 31/022* (2013.01); *A61L 31/14* (2013.01); *A61H 2201/1207* (2013.01); *A61H 2201/5005* (2013.01); *A61H 2201/5069* (2013.01); *A61H 2201/5082* (2013.01); *A61H 2230/50* (2013.01); *A61L 2400/16* (2013.01)

(58) Field of Classification Search
CPC ........ A61H 19/00; A61H 19/30; A61H 19/34; A61H 19/40; A61H 19/44; A61H 19/50; A61H 21/00; A61H 23/00
See application file for complete search history.

(56) References Cited

U.S. PATENT DOCUMENTS

| | | | |
|---|---|---|---|
| 6,190,307 B1 | 2/2001 | Tsai | |
| 7,438,681 B2 * | 10/2008 | Kobashikawa | ........ A61H 19/34 600/38 |
| 8,496,572 B2 * | 7/2013 | Lee | ........ A61H 19/34 600/38 |
| 8,936,544 B2 | 1/2015 | Shahoian | |
| 9,615,994 B2 | 4/2017 | Sedic | |
| 2010/0041944 A1 * | 2/2010 | Levy | ........ A61H 19/32 600/38 |
| 2011/0133910 A1 | 6/2011 | Alarcon | |

(Continued)

*Primary Examiner* — John P Lacyk
(74) *Attorney, Agent, or Firm* — Wooshik Shim; Thomas E. LaGrandeur; Bold IP, PLLC

(57) ABSTRACT

A personal therapy device, directed generally to an elongated sexual stimulation device for female use having advanced shape motion control and shape transformation. In one embodiment, the device has a flexible outer body elongated in a longitudinal direction and a shape memory alloy (SMA) thrust actuator disposed within the flexible outer body. In another embodiment, the device includes one or more skeletal segments which are disposed within the flexible outer body and capable of deformation in various directions. In yet another embodiment, the device includes one or more rotational servo motor pair units, where each rotational servo motor of the rotational servo motor pair has an eccentric weight, and the synchronized rotation of the eccentric weight pair generates a net lateral wobbling motion. In yet another embodiment, the device includes an external positioning sensor unit, an inertial measurement unit, one or more pressure sensors, or a combination thereof.

20 Claims, 9 Drawing Sheets

(56) References Cited

U.S. PATENT DOCUMENTS

2013/0281776 A1\* 10/2013 Levy ..................... A61F 5/41
                                                        600/38
2015/0359703 A1   12/2015 Richardson, II
2016/0354277 A1\* 12/2016 Fima ..................... A61H 19/44
2017/0281459 A1   10/2017 Cirillo-Schmidt \* cited by examiner

PERSONAL THERAPY DEVICE UTILIZING SHAPE TRANSFORMATION AND ADVANCED MOTION CONTROL

CROSS-REFERENCE TO RELATED APPLICATIONS

This application claims priority to U.S. Provisional Application No. 62/670,652 filed May 11, 2018.

TECHNICAL FIELD

The present description includes embodiments generally directed to a personal therapy device. More specifically, the embodiments are directed generally to an elongated sexual stimulation device for female use having advanced shape motion control and shape transformation.

BACKGROUND

Sexual stimulation devices, often called sex toys, apply forces or vibrations to a portion of a person's body to arouse sexual stimulation. Some devices are passive, meaning that they do not generate any motion by itself and are supposed to be manipulated by a user's hand. These devices demand constant control of movements by their users, so that users are distracted from focusing on taking pleasures.

Aiming at achieving maximum user satisfaction, some devices in the market provide active movements. For example, such active movements include vibrational movements, where outer surfaces of the device transfer vibrational movements on the user's skin. In order to generate vibration, some devices use an electric motor that rotates an eccentric weight. In another example, a piezoelectric modulator is used.

Some devices in the market provide shape change capabilities. In one example, an elongated stimulation device for female users is capable of changing its size in the longitudinal direction, or making a thrust motion operated by a battery-powered motor. In another example, an elongated stimulation device has one end portion of the elongated device capable of slowly rotating around the longitudinal axis along the elongated direction as if the end portion orbits around its axial center. This movement is intended to enhance the contact with and pressure on the inner skin of a female's body and thereby increase the sexual pleasure of the female.

Some elongated stimulation devices in the market include various types of sensors such as temperature sensors and pressure sensors. In one example, a temperature sensor is used to measure temperature on the surface of the device. If the device enters a female body such as vagina, the temperature rises up to the human body temperature and the device is triggered to operate. In another example, a series of pressure sensors located around the surface of the device measure pressures applied between the device and the skin of the female body. In still another example, a three-dimensional position angular sensor detects the angular orientation of the device with respect to the external environment or gravity. Instead of pressing buttons to change modes of operation, a user can change the orientation of the device in a predetermined way and turn on or off the device or change its mode of operation.

However, a device having more versatile movements beyond simple vibrational, linear thrust and rotational orbiting movements is needed. Moreover, a device that is capable of independently operating interactively responding to its relative location with respect to a user's body with minimal human intervention is needed, so that a user can be fully immersed in the enjoyment of the device without being distracted by constantly having to adjust and manipulate the device.

SUMMARY

This Summary is provided to introduce a selection of representative concepts in a simplified form that are further described below in the Detailed Description. This Summary is not intended to identify key features or essential features of the claimed subject matter, nor is it intended to be used in any way that would limit the scope of the claimed subject matter.

A device having more versatile movements beyond simple vibrational, linear thrust, lateral and rotational orbiting movements is needed. Moreover, a device that is capable of independently operating interactively responding to its relative location with respect to a user's body with minimal human intervention is needed, so that a user can be fully immersed in the enjoyment of the device without being distracted by constantly having to adjust and manipulate the device.

In one embodiment, a personal therapy device has a flexible outer body elongated in a longitudinal direction and a shape memory alloy (SMA) thrust actuator disposed within the flexible outer body. The flexible outer body has a substantially cylindrical shape. The SMA thrust actuator may include one or more shape memory alloy (SMA) wires. The SMA thrust actuator may change its length along the longitudinal direction of the personal therapy device when the SMA wires are deformed by applying electric current through the SMA wires.

In another embodiment, a personal therapy device has a flexible outer body elongated in a longitudinal direction and one or more skeletal segments disposed within the flexible outer body. The skeletal segment includes two disc-shaped plates substantially coaxially spaced apart from each other along the longitudinal direction, conforming to the shape of the flexible outer body. One or more shape memory wires connect the two plates. The shape memory wires may connect the outer rims of the two plates, or they may connect the inner portions of the two plates.

In yet another embodiment, a personal therapy device has a flexible outer body elongated in a longitudinal direction and a lateral movement mechanism. The lateral movement mechanism may have a pair of rotational servo motors with a pair of eccentric weights. The synchronized rotation of the eccentric weight pair generates a net linear wobbling motion.

In yet another embodiment, a personal therapy device has an external positioning sensor unit, an inertial measurement unit, one or more pressure sensors, or a combination thereof. A control unit electrically connected with the above units and pressure sensors enables an interactive motion control of the personal therapy device in response to various dispositions of the personal therapy device with respect to the external environment. The control unit may be controlled wirelessly by a mobile app installed onto a mobile device.

Other aspects and advantages of the invention will be apparent from the following description and the appended claims.

BRIEF DESCRIPTION OF DRAWINGS

The present invention will be described by way of exemplary embodiments, but not limitations, illustrated in the accompanying drawings in which like references denote similar elements, and in which.

DETAILED DESCRIPTION

Figure 1:
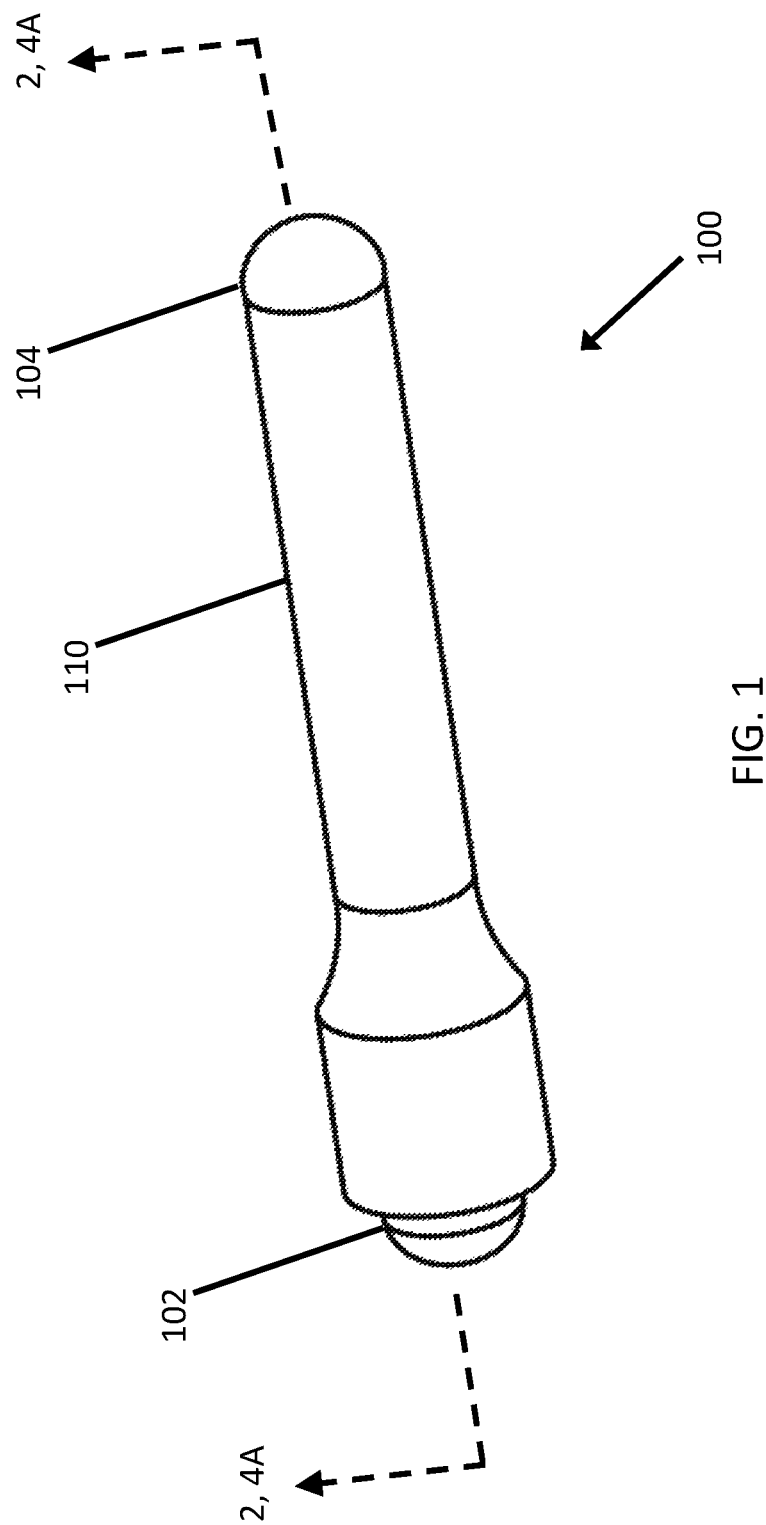
FIG. 1 is a perspective view of a personal therapy device in accordance with an illustrative embodiment.

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

As a preface to the detailed description, it should be noted that, as used in this specification, the singular forms "a," "an," and "the" include plural referents, unless the context clearly dictates otherwise. Like reference numbers and designations in the various drawings indicate like elements.

The present description includes one or more embodiments that are generally related to a personal therapy device for sexual enjoyment of a user. Further, the present description includes one or more embodiments that include at least one of the following elements: (1) one or more rib segments, each rib including one or more shape memory alloy (SMA) wires whose lengths and angles may be changed by a controller, thereby changing the angle or shape of the segment; (2) a lateral movement mechanism; and (3) an external position sensing device capable of measuring the external position and the orientation of the device. The one or more embodiments may have a combination of the above elements, as well as other elements that will be described in more detail below.

FIG. 1 is a perspective view of an exemplary embodiment of a personal therapy device 100. The device 100 represents a basic model and has a flexible outer body 110 elongated in a longitudinal direction. Personal therapy device 100 includes a proximal end 102 and a distal end 104 as shown in FIG. 1. In one or more embodiments, flexible outer body 110 forms the outside surface of the device 100 and may be made waterproof and completely enclose the other parts of the device to protect them under its surface from being damaged. Many parts are disposed inside flexible outer body 110, including an internal skeletal structure 120, a lateral movement mechanism 130, and a sensor network 140, that are not shown in FIG. 1 but will be described in more detail below. Sensor network 140 may have one or more temperature sensors, one or more pressure sensors, and/or one or more gyroscopes or gravitational sensors. Device 100 also has a control unit 170, preferably located near proximal end 102.

Flexible outer body 110 is elongated in a longitudinal direction 105 and preferably has a substantially cylindrical shape, but it may have any other shape in alternative embodiments. For example, flexible outer body 110 has an elongated shape and diameter suitable to be inserted into a vagina of an adult female. Distal end 104 of personal therapy device 100 is in a convex shape, preferably in a spherical or ellipsoidal shape or its variant so as to provide smooth contact between device 100 and the inner skin such as the inner wall of the vagina of an adult female. Flexible outer body 110 may be made of a flexible material such as silicone, latex, thermoplastic elastomers or the like in some embodiments, although any material known in the art may be used as needed. Further, in some embodiments, pressure sensors in the form of pressure sensitive fabric, which is part of sensor network 140, may also encompass flexible outer body 110, as will be further detailed below.

Figure 2:
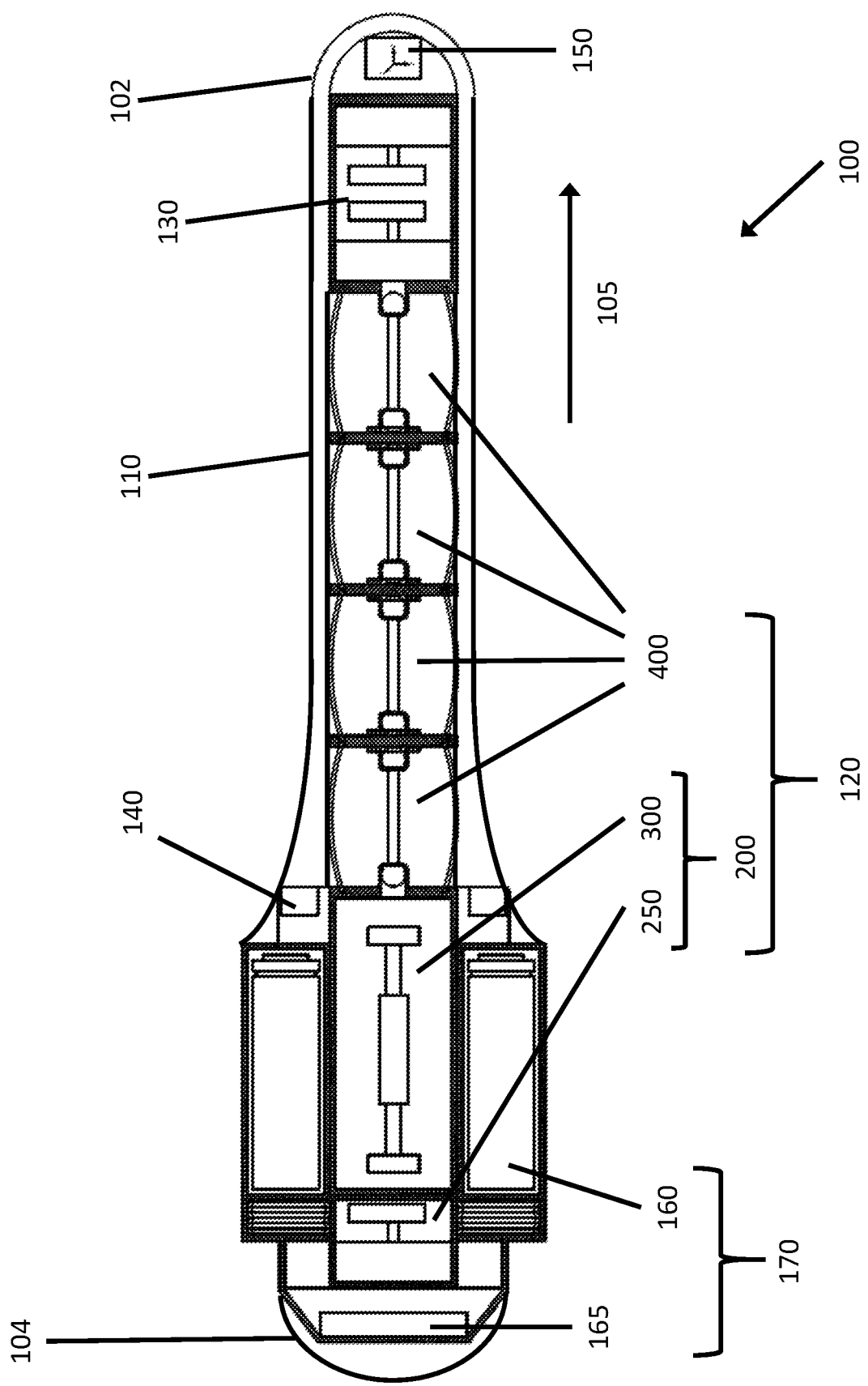
FIG. 2 is a sectional side view of the personal therapy device of FIG. 1 taken along line 2-2 shown in FIG. 1.

FIG. 2 shows a sectional side view of the exemplary personal therapy device 100 taken along the line 2-2 of FIG. 1. An internal skeletal structure 120, a lateral movement mechanism 130, a sensor network 140, and a control unit 170 are shown in FIG. 2. Control unit 170 may further include a power supply unit 160 and a control circuitry 165 and may be, for example, located on a proximal end 102 of device 100, which is on the opposite side of distal end 104 of device 100, as shown in FIG. 2. Alternatively, power supply unit 160 and control circuitry 165 may be separately located from each other in any other location suitable for the operation of device 100.

Internal skeletal structure 120 is disposed inside the elongated shape of flexible outer body 110. In one or more embodiments, internal skeletal structure 120 may include one or more ribs 400. In some embodiments, internal skeletal structure 120 may also have a linear thrust motion unit 200, which may be a separate unit from ribs 400 or integrated into ribs 400. Likewise, lateral movement mechanism 130 may be a separate unit from ribs 400 or integrated into ribs 400, as further described below.

In one embodiment, linear thrust motion unit 200 may include a linear DC servo motor. Linear DC servo motor may be operated by a mechanism known to a person of skill in the art including pneumatic, electromechanical, and electromagnetic operation mechanisms. By this operation, a linear DC servo motor may generate a linear thrust motion by change of length of device 100 in longitudinal direction 105. For example, the frequency of the linear thrust motion may range from a few tenths of a Hertz to a few hundred Hertz. In one embodiment, linear thrust motion unit 200 may include a linear servo motor 250 connected with a gear train (not shown). The gear train transforms the rotational motion of linear servo motor 250 into a cyclic thrust motion in the longitudinal direction 105 as known to a person of skill in the art. For example, linear motor 250 may have a cam structure attached to the rotor of linear motor 250 and generate a linear thrust motion. Power supply unit 160 is electrically connected to linear thrust motion unit 200 and supplies power to linear servo motor 250. Control unit 170 controls turning on/off and controlling the speed and direction of the thrust motion of linear thrust motion unit 200 and/or ribs 400.

Figure 3:
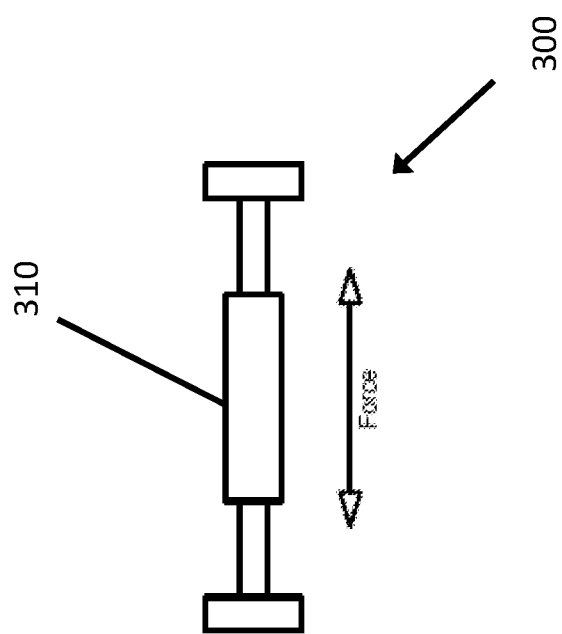
FIG. 3 is a side view of an exemplary SMA thrust actuator.

In another embodiment, linear thrust motion unit 200 may include a shape memory alloy (SMA) thrust actuator 300 disposed within flexible outer body 110. FIG. 3 is a side view of an exemplary SMA thrust actuator 300 used as linear thrust motion unit 200. A shape memory alloy is an alloy that remembers its original shape and that when deformed returns to its pre-deformed shape by heating or cooling. Such deformation by heating can be done by applying an electric current through the SMA. An SMA material is made from combining various materials. Such combinations include, but are not limited to, copper-aluminum-nickel, nickel-titanium (NiTi), and zinc-copper-gold-iron. The threshold temperature at which the SMA is deformed may be determined by, for example, adjusting the ratio of the alloys in the SMA. Accordingly, the threshold electric current and time for which the current flows through the SMA associated with the threshold temperature may subsequently be determined.

SMA thrust actuator 300 may include one SMA wire/rod 310 extending along longitudinal direction 105 as shown in FIG. 2. In one embodiment, SMA wire/rod 310 is electrically connected to power supply unit 160 and control unit 170, and its length changes according to the electrical current applied to it through power supply unit 160 and control unit 170. Alternatively, SMA thrust actuator 300 may include two or more SMA wires symmetrically disposed around longitudinal direction 105. Each of the SMA wires may be bent in one direction or another, so that when the SMA wires are bent together they collectively make a deformation of linear thrust actuator 300 in longitudinal direction 105. When linear thrust motion unit 200 changes its length in longitudinal direction 105, the overall length of device 100 in longitudinal direction 105 changes accordingly.

In another embodiment, the internal skeletal structure 120 includes one or more ribs 400 disposed within flexible outer body 110. For embodiments where more than one of such a linear thrust motion unit 200 and ribs 400 are disposed in the device 100, each of them may be connected along the longitudinal direction 105 such that their linear deformation in the longitudinal direction 105 may add up. For example, in FIG. 2 linear thrust motion unit 200 is disposed on proximal end 102 of device 100, and a plurality of ribs 400 are physically connected to linear thrust motion unit 200 and disposed towards a distal end 104 of device 100. Device 100 may include only one rib 400 or as many ribs 400 as needed in order to achieve sufficient deformation as described in more detail below.

Figure 4B:
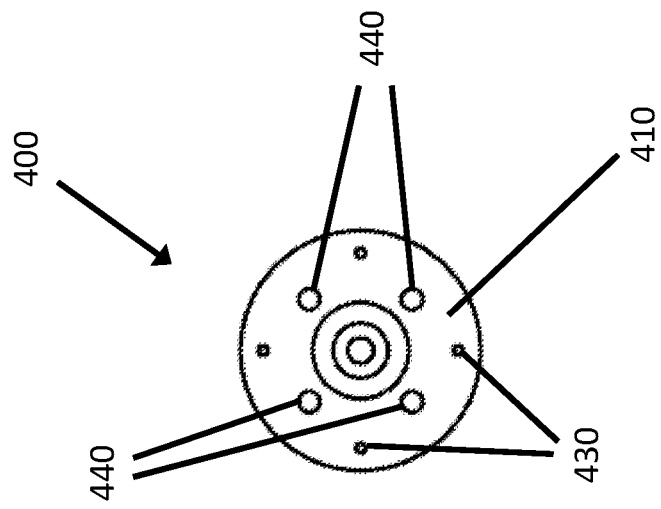
FIG. 4B is a front view of the first exemplary skeletal segment of FIG. 4A
Figure 4A:
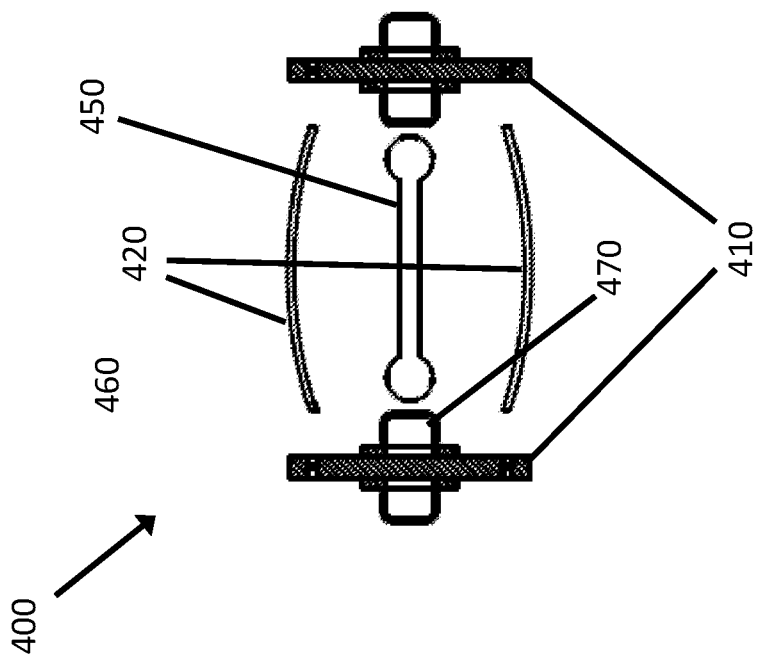
FIG. 4A is a sectional side view of a first exemplary skeletal segment taken along line 4A-4A shown in FIG. 1.

FIGS. 4A and 4B respectively show a sectional side view taken along the line 4A-4A of FIG. 1 and a front view of an exemplary rib 400. In this embodiment shown in FIGS. 4A-4B, each of the ribs 400 includes a pair of disc-shaped plates 410 substantially coaxially spaced apart from each other along longitudinal direction 105, conforming to the shape of flexible outer body 110. One or more shape memory alloy (SMA) muscle wires 420 connect the two disc-shaped plates 410. Each of the SMA muscle wires 420 may connect the two disc-shaped plates 410 at its ends of the SMA muscle wire 420 by being tied to a SMA joint 430 on each of the disc-shaped plates 410. Alternatively, each of the SMA muscle wires 420 may pass through a through hole 440 on one of the disc-shaped plates 410 such that a set of long SMA muscle wires 420 runs parallel to one another in longitudinal direction 105 connecting proximal end 102 and distal end 104 of device 100.

In some embodiments, SMA muscle wires 420 may have various shapes, including but not limited to, a thin wire elongated along longitudinal direction 105 of device 100, a thin sheet elongated along longitudinal direction 105, a thick sheet, and a cylinder. In embodiments where SMA muscle wires 420 connect the two disc-shaped plates 410 with SMA joints 430, the length of each SMA muscle wires 420 determines the separation between disc-shaped plates 410 and thereby the length of one of the ribs 400.

SMA muscle wires 420 may be individually and/or collectively deformed by applying current through each of the SMA muscle wires 420, or otherwise heating and cooling SMA muscle wires 420 using any other methods known in the art. In some embodiments, control unit 170 may measure the temperatures of the SMA muscle wires 420 through SMA temperature sensors (not shown) and use a feedback loop to monitor and control the deformation and restoration of the shapes of SMA muscle wires 420.

When SMA muscle wires 420 are uniformly deformed, the length of one of the ribs 400 changes, thereby effectively providing a linear thrust motion in longitudinal direction 105. Alternatively, when SMA muscle wires 420 are not uniformly deformed, two disc-shaped plates 410, which may be originally substantially parallel to each other, are tilted with respect to each other, thereby bending the shape of device 100. Therefore, SMA muscle wires 420 may be configured such that device 100 may be bent in many different desired directions. Control unit 170 electrically connected to SMA muscle wires 420 controls the deformation of SMA muscle wires 420.

In some embodiments, a backbone 450 may be located at the axial center of the two disc-shaped plates 410 along longitudinal direction 105. Backbone 450 sustains the separation of the two disc-shaped plates 410 and roughly defines the length of a rib 400. In a non-limiting embodiment, a backbone end 460 of backbone 450 may have an ellipsoidal contour, and its corresponding disc-shaped plate 410 may have a receptacle 470 having a matching concave contour such that receptacle 470 receives the backbone end 460 and backbone 450 pivotably can move with respect to receptacle 470. This configuration enables tilting of the angle between the two disc-shaped plates 410 within a rib 400, in accordance with SMA muscle wires 420 that can bend in many different desired directions as described above.

Disc-shaped plates 410 and backbones 450 may be made out of material having stiffness enough to sustain the structure of device, including plastic, ceramic, and stainless steel.

Figure 4C:
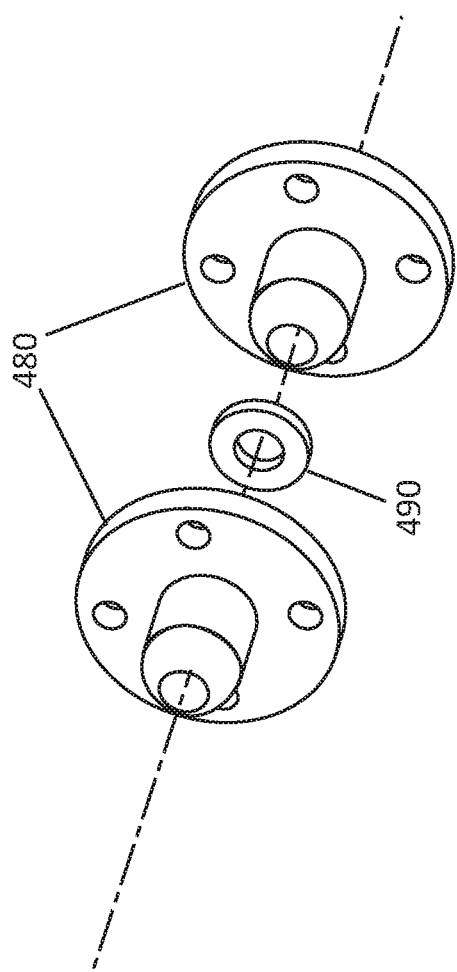
FIG. 4C is an exploded perspective view of a second exemplary skeletal segment.
Figure 4D:
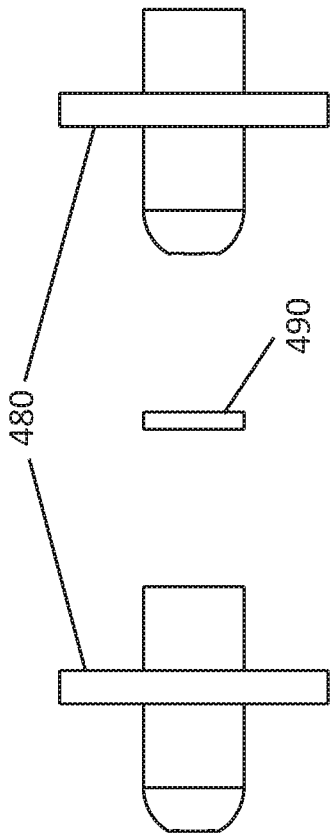
FIG. 4D is a side view of the second exemplary skeletal segment of FIG. 4C

In some embodiments, a disc-shaped plate 410 and a backbone 450 may be one piece. In some other embodiments, backbones 450 may have hollow passages through their axial centers. Referring to FIG. 4C, an exploded perspective view of an exemplary rib 400 is shown. FIG. 4D is a side view of the exemplary rib 400 of FIG. 4C. In this embodiment shown in FIGS. 4C-4D, each of the two combination ribs 480 has a protrusion on each side of the disc-shaped part in lieu of a backbone. The combination ribs 480 are configured to be assembled together with a cushion 490 between them. As shown in FIG. 4C, the axial centers of combination ribs 480 and cushion 490 are hollow with through holes such that electrical wires (not shown) may go through these holes to connect SMA muscle wires 420 and other sensors from control unit 170. Cushion 490 may be made out of wear-resistant plastic or any other wear-resistant material and is inserted between the combination ribs 480 to facilitate easy tilting of one of the combination ribs 480 with respect to another.

Figure 5A:
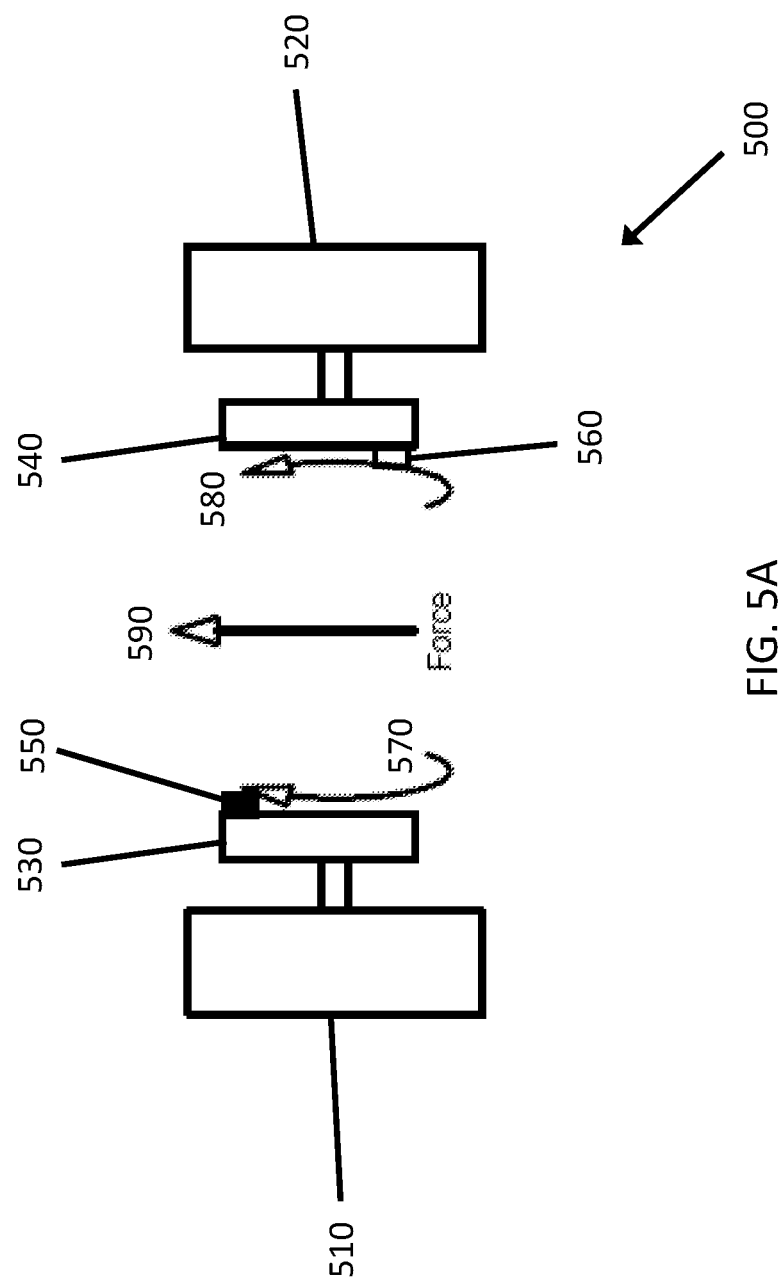
FIG. 5A is a side view of an exemplary lateral movement mechanism.

Referring to FIG. 5A, a side view of an exemplary lateral movement mechanism 130 located close to distal end 104 of device 100 is shown. In one embodiment, the lateral movement mechanism 130 has one or more rotational servo motor pairs 500, each pair comprising a first rotational servo motor 510 and a second rotational servo motor 520. In one embodiment, each of the first and the second rotational servo motors 510, 520 has an eccentric weight 550, 560 attached to a rotating disc 530, 540 and rotating around the axis of rotation of each motor 510, 520, respectively. First and second rotational servo motors 510, 520 are disposed coaxially along longitudinal direction 105 of device 100, and the axis of rotation of first rotational servo motor 510 is the opposite of the axis of rotation of second rotational servo motor 520. In other words, the two eccentric weights 550 and 560 rotate in opposite directions to each other, as indicated by arrows 570 and 580.

First and second rotational servo motors 510, 520 are electrically connected to control unit 170 as shown in FIG. 2. Control unit 170 is capable of controlling the speeds and directions of rotation of first and second rotational servo motors 510, 520. For example, control unit 170 is capable of rotating eccentric weights 550, 560 in-sync with each other, such that, eccentric weights 550, 560 rotate at the same speed but in opposite directions. In the in-sync mode of rotation, the synchronized rotation of eccentric weights 550, 560 generate a net linear wobbling motion. The direction of the linear wobbling motion is perpendicular to longitudinal direction 105. The speed of the rotation controlled by control unit 170 determines the frequency of the wobbling. For example, the frequency of the wobbling may range from a few Hertz to a few hundred Hertz.

Figures 5B, 5C, 5D:
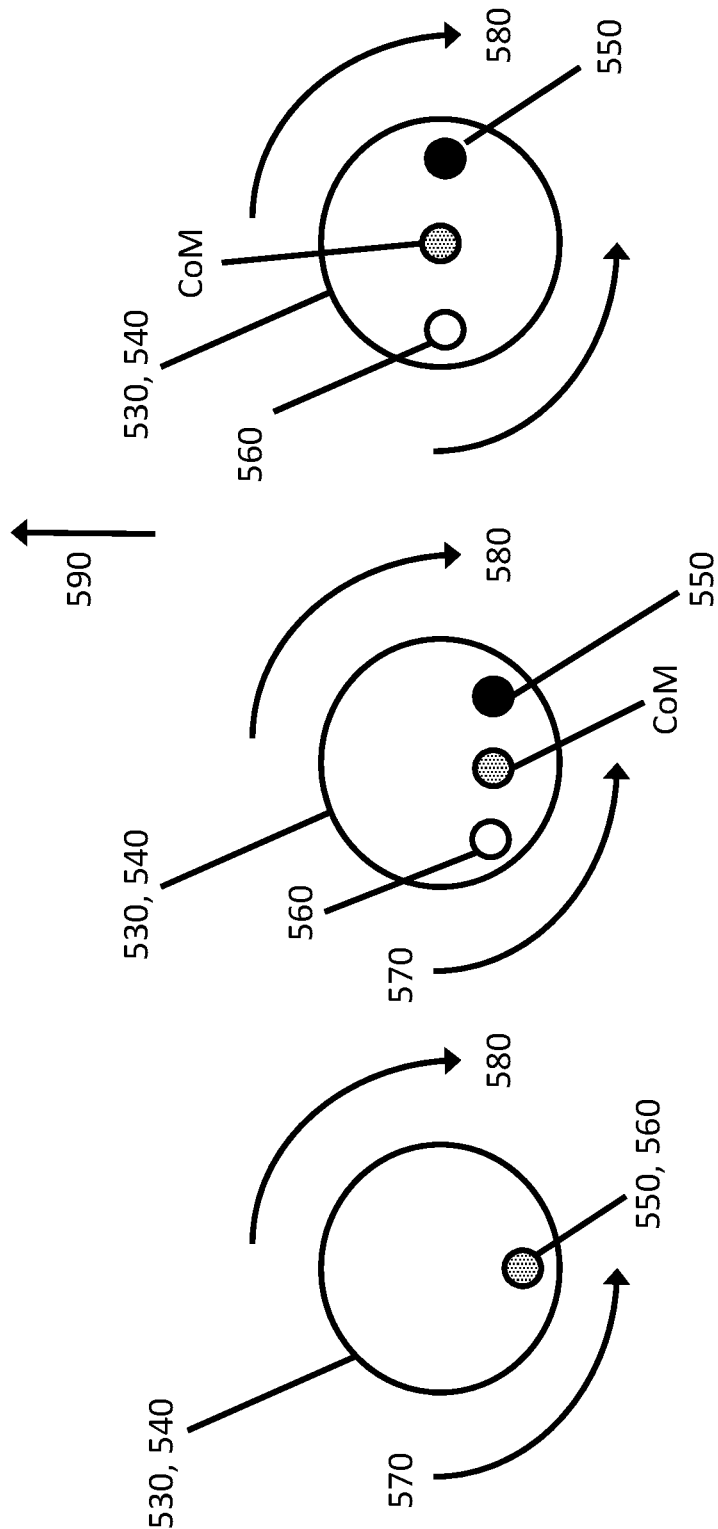
FIGS. 5B-5D are an illustration of the mode of operation of the exemplary lateral movement mechanism of FIG. 5A.

FIGS. 5B-5D further illustrate how lateral movement mechanism 130 generates lateral movement. Viewed in longitudinal direction 105, rotating discs 530 and 540 coincide, and as indicated by arrows 570, 580, rotating discs 530, 540 rotate at the same angular speed as each other but in the counter-clockwise and clockwise directions, respectively.

Initially in FIG. 5B, the locations of eccentric weights 550, 560 coincide at the bottom of the discs, and their center of mass (CoM) is also at the bottom of the discs. After a certain time, as in FIG. 5C, eccentric weights 550, 560 separate each other as they rotate counter-clockwise and clockwise, respectively. Accordingly, their CoM moves in the direction of force 590. Further later, as in FIG. 5D, eccentric weights 550, 560 move further and the CoM moves further up. In this way, the CoM oscillates back and forth in the direction of force 590 and thereby a lateral movement is generated. To change the direction of force 590, one can briefly desynchronize the mutual rotation of rotating discs 530, 540 by changing the angular speed of one of the discs, change the location where the two eccentric weights 550, 560 coincide on the discs 530, 540, and re-synchronize the mutual rotation. Such operations are made possible by control unit 170. Control unit 170 is configured to generate various modes of movements including linear lateral movement and rotational lateral movement.

In one exemplary mode of operation of device 100, when control unit 170 briefly breaks the in-sync mode of rotation by changing the rotational speed of one of the eccentric weight 550 with respect to the other eccentric weight 560 and then restores the synchronization by matching the rotational speeds of the two eccentric weights, the direction of the linear wobbling motion may be changed. In another exemplary mode of operation, by controlling the two rotational servo motors slightly out-of-sync, in other words, by slightly mismatching the relative rotational speeds of two eccentric weights 550, 560, the direction of the linear wobbling motion may be made to slowly change in time, resulting in a wobbling motion whose direction of wobbling slowly changes in a clockwise or counterclockwise direction around longitudinal direction 105. In still another exemplary mode of operation, by changing the relative speeds of eccentric weights 550, 560, control unit 170 may make the rotational servo motors 510 and 520 generate a random vibrational motion.

Referring back to FIG. 2, in one embodiment, device 100 may have an external positioning sensor unit 140. Although in FIG. 2 external positioning sensor unit 140 is shown to be disposed between the linear thrust motion unit 200 and ribs 400, it may be disposed in any position inside or on the surface of device 100. External positioning sensor unit 140 includes one or more external positioning sensors. In one embodiment, one external positioning sensor may be disposed at distal end 104 and another external positioning sensor may be disposed at proximal end 102. External positioning sensor unit 140 is electrically connected with controller 170. Each external positioning sensor measures an external position of device 100 in at least one dimension. Control unit 170 receives the measured external position values and controls other parts of device 100, such as, for example, internal skeletal structure 120 and lateral movement mechanism 130, so that the motions of device 100 in response to the measured external position values may increase sexual pleasure of the user.

For example, external positioning sensor unit 140 has an external positioning sensor that measures the external position values of device 100 in X, Y, and Z dimensions, where the X, Y, and Z dimensions are perpendicular to one another. In another example, external positioning sensor unit 140 may include a global positioning system (GPS) sensor unit.

External positioning sensor unit 140 may also include one or more three-dimensional angular sensors that measure the three-dimensional angular disposition of device 100. In this example, control unit 170 may be programmed to select a desired position and/or angle of the device 100, so that when the position or angle of device 100 is changed control unit 170 can move the other parts of device 100, such as internal skeletal structure 120 and lateral movement mechanism 130 to adjust or correct its disposition. Each of the three-dimensional angular sensors may include a gyroscope. For example, one embodiment may have one external positioning sensor having a gyroscope disposed at distal end 104 and another external positioning sensor having another gyroscope disposed at proximal end 102. The two gyroscopes at distal end 104 and proximal end 102 may detect and monitor the orientation of device 100 with respect to the environment. The two gyroscopes may also detect and monitor the relative orientation of distal end 104 with respect to proximal end 102 to provide feedback signal to control unit 170. For example, when the desired mode of operation of device 100 is bending distal end 104 with respect to proximal end 102 by 10 degrees in one direction, control unit 170 controls the current through one or more SMA muscle wires 420 until the 10 degrees bending is achieved and maintains such a disposition using a feedback loop.

In another example, external positioning sensor unit 140 includes a temperature sensor. In this example, when a portion of device 100 enters a user's body or is pulled out of the user's body, the temperature sensor of external positioning sensor unit 140 measures the change in temperature on the surface of device 100 and enables control unit 170 to operate other parts of device 100 such as internal skeletal structure 120 and/or lateral movement mechanism 130 so that the degree of insertion of device 100 into the user's body, the lateral movement, and/or the vibrational movement of device 100 may be controllable.

Still referring to FIG. 2, in one embodiment, device 100 may have an inertial measurement unit 150. In some embodiments, external positioning sensor unit 140 and inertial measurement unit 150 may be combined together to form one unit. Although in FIG. 2 inertial measurement unit 150 is shown to be disposed at distal end 104 of device 100, it may be disposed in any position inside or on the surface of the device 100. Inertial measurement unit 150 measures the acceleration of device 100, preferably the acceleration of distal end 104 of device 100 in one or more dimensions. In one embodiment, similarly to external positioning sensor unit 140, inertial measurement unit 150 may include one inertial sensor at distal end 104 and another inertial sensor at proximal end 102. Control unit 170 is electrically connected to inertial measurement unit 150, and it receives the measured acceleration from inertial measurement unit 150 and operates other parts of device 100 such as internal skeletal structure 120 and lateral movement mechanism 130 so that the linear thrust motion or rotational motion inside the user's body may be controllable. For example, control unit 170 may receive the acceleration of device 100 measured by inertial measurement unit 150 in combination with the orientation of device 100 measured by external positioning sensor unit 140 and adjust the angular disposition and movement of device 100.

In some embodiments, device 100 may have one or more pressure sensors (not shown). The pressure sensors may be disposed on or near the surface of flexible outer body 110. Multiple pressure sensors may be spread over a large area of flexible outer body 100 in the form of a pressure sensitive fabric. The pressure sensors measure pressures on the surface of flexible outer body 110. When the area around a pressure sensor makes contact with a user's body, control unit 170 controls the motion of device 100 so that device 100 is adjusted to exert the most desirable pressure, vibration, and/or movement upon the user's skin for increased pleasure of the user.

Control unit 170 includes a microprocessor (not shown) and a storage including a memory (not shown) and is electrically connected to the parts described above and receives various signals from sensors including external positioning sensor unit 140, inertial measurement unit 150 and pressure sensors. Control unit 170 also controls the movements of various units including internal skeletal structure 120 and rotational servo motor pair unit 130 to maximize the enjoyment of the user. In some embodiments, control unit 170 may be a microcontroller.

Control unit 170 may be able to be externally programmed. For example, a set of external buttons may be disposed on the surface of device 100 and electrically connected to control unit 170 so that a user may select a desired mode of operation from a set of pre-programmed sequence of movements of device 100 stored in the memory. In another example, control unit 170 may be programmable to perform a sequence of movements by a control mobile app downloaded to a mobile device. A user may program device 100 using a graphical user interface (GUI) of the control mobile app. Control unit 170 includes a wireless communication unit capable of communicating with mobile devices onto which the control mobile app is installed. The wireless communication may be made using WiFi, Bluetooth, telephone network, or any other technology that is known to a person having ordinary skill in the art.

The parts that require electric power including internal skeletal structure 120, lateral movement mechanism 130, external positioning sensor unit 140, inertial measurement unit 150 and control unit 170 are connected to and powered by a power supply unit 160. Power supply unit 160 may include one or more batteries. The one or more batteries may be charged by connecting power supply unit 160 to a conventional external electric outlet. Alternatively, the one or more batteries may be wirelessly charged using a wireless charging technique known to a person of ordinary skill in the art or, in other embodiments, disposable, replaceable batteries may be used.

Figure 6A:
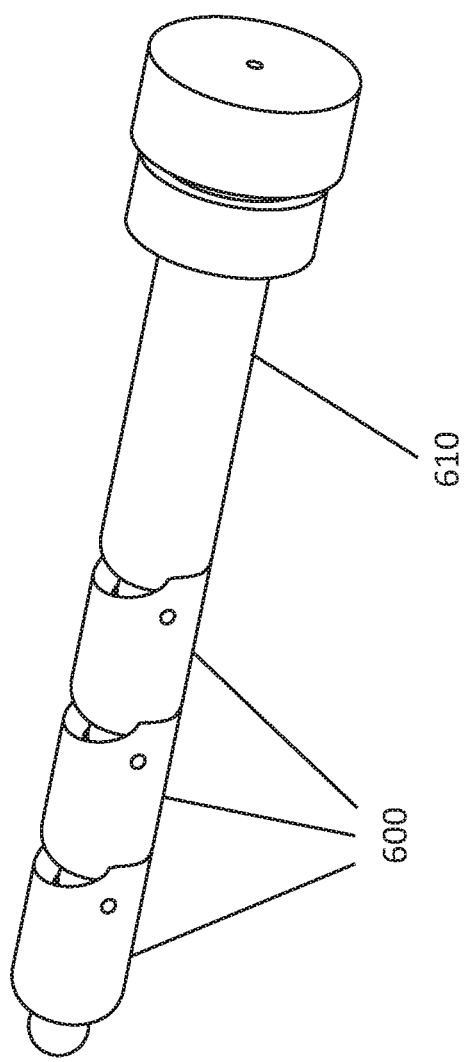
FIG. 6A is a perspective view of protective shells in a straight state in accordance with an illustrative embodiment.

Electrically connecting the above parts with control unit 170 may be done by running internal electrical wires. In one exemplary embodiment, such electrical wires run through the center of internal skeletal structure 120. Referring to FIG. 6A, a perspective view showing the internal skeletal structure 120 of such an embodiment of a personal therapy device 100 is shown.

In some embodiments, there may be one or more protective shells underneath flexible outer body 110. Referring to FIG. 6A, a perspective view of protective shells 600 and a base shell 610 enclosing internal skeletal structure 120 (shown in FIG. 2) of device 100 are shown. Each of the protective shells 600 is in corresponding location with a rib 400 to facilitate bending controlled by control unit 170. Device 100 shown in FIG. 6A has three protective shells 600, but a different number of protective shells 600 may be used.

Figure 6B:
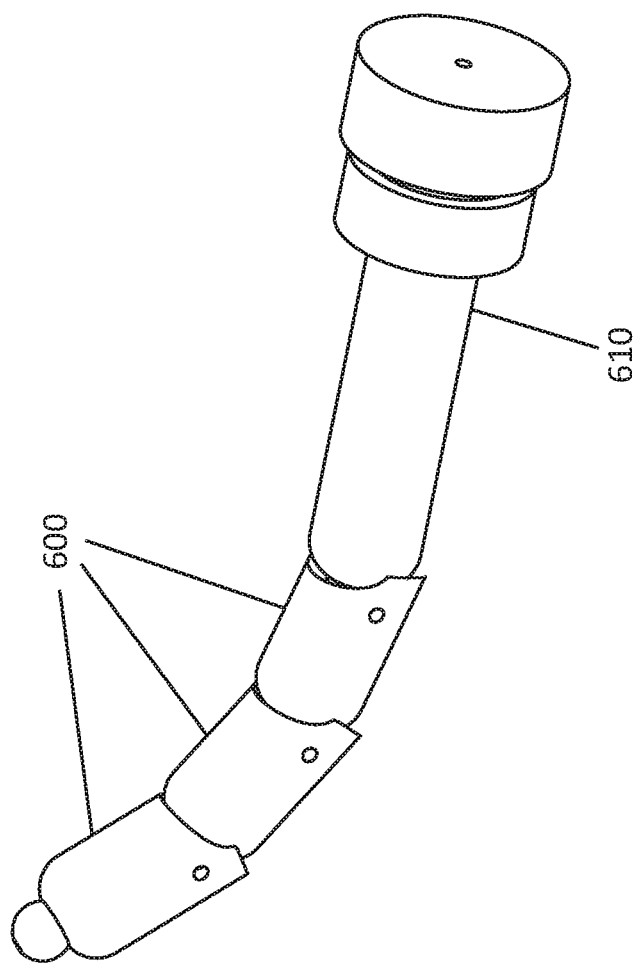
FIG. 6B is a perspective view of protective shells of FIG. 6A in a bent state.

Referring to FIG. 6B, a perspective view of the embodiment shown in FIG. 6A is shown with each of the protective shells 600 bent in one direction. Bending in only one direction is shown in FIG. 6B as an illustration, but bending in various degrees of freedom may be possible.

Bending by tilting one protective shell with respect to another protective shell may be achieved in various ways known to a person of ordinary skill in the art. Although not shown in FIGS. 6A-6B in detail, one way of such bending is to make a spherical protrusion at one end of the first protective shell and to make a concave spherical receptacle at the other end of the second protective shell.

While certain exemplary embodiments have been described and shown in the accompanying drawings, it is to be understood that such embodiments are merely illustrative of and not restrictive on the broad application, and that this application is not limited to the specific constructions and arrangements shown and described, since various other modifications within the spirit of the present invention may occur to those of ordinary skill in the art.

What is claimed is:

1. A personal therapy device comprising:
   a flexible outer body elongated in a longitudinal direction defining a length and having a proximal end and a distal end;
   one or more ribs disposed within the flexible outer body, wherein each of the ribs comprises
      at least two plates spaced apart from each other along the longitudinal direction, each of the two plates having a substantially flat surface aligned substantially parallel with each other and substantially perpendicular to the longitudinal direction, and
      one or more shape memory wires disposed between the two plates and connected to the two plates;
   a controller, wherein the controller is electrically connected to the shape memory wires; and
   a power source configured to provide electric power.

2. The personal therapy device of claim 1, wherein the controller is configured to cause deformation of the one or more shape memory wires.

3. The personal therapy device of claim 2, wherein the controller uses electrical current through the one or more shape memory wires to cause deformation.

4. The personal therapy device of claim 2, wherein the controller uses heat through the one or more shape memory wires to cause deformation.

5. The personal therapy device of claim 4, further comprising one or more wire temperature sensors configured to measure the temperature of at least one of the one or more shape memory wires.

6. The personal therapy device of claim 1, further comprising a lateral movement mechanism electrically connected to the controller.

7. The personal therapy device of claim 6, wherein the lateral movement mechanism comprises a pair of rotational servo motors, wherein each rotational servo motor has an eccentric weight.

8. The personal therapy device of claim 7, wherein the controller is connected to the pair of rotation servo motors and capable of generating one or more modes of operation of the lateral movement mechanism by rotating the two eccentric weights synchronized and desynchronized with respect to each other in opposite directions.

9. The personal therapy device of claim 6, further comprising an inertial measurement unit capable of measuring one or more acceleration values.

10. The personal therapy device of claim 9, wherein the controller is configured to generate one or more modes of operation of the lateral movement mechanism in response to the measured acceleration values.

11. The personal therapy device of claim 1, further comprising a linear thrust motion unit electrically connected to the controller and configured to change the length of the flexible outer body in the longitudinal direction.

12. The personal therapy device of claim 1, further comprising one or more protective shells disposed within the flexible outer body and substantially enclosing the one or more ribs.

13. The personal therapy device of claim 1, further comprising one or more inertial measurement unit capable of measuring one or more acceleration values.

14. The personal therapy device of claim 13, wherein the controller is configured to generate an electrical control signal through the one or more shape memory wires in response to the measured acceleration values.

15. The personal therapy device of claim 1, further comprising an external position sensing unit capable of measuring one or more external position values of the personal therapy device and an orientation of the longitudinal direction of the personal therapy device.

16. The personal therapy device of claim 15, wherein the controller is configured to generate an electrical control signal through the one or more shape memory wires in response to the measured external position value.

17. The personal therapy device of claim 15, wherein the external position sensing unit comprises one or more angular position sensors.

18. The personal therapy device of claim 15, wherein the external position sensing unit comprises a global positioning system (GPS) sensor.

19. The personal therapy device of claim 1, further comprising a pressure measurement unit capable of measuring one or more pressure values at one or more pressure points.

20. The personal therapy device of claim 1, further comprising a body temperature sensing unit.

* * * * *